United States Patent [19]
Socci et al.

[11] Patent Number: 6,139,822
[45] Date of Patent: Oct. 31, 2000

[54] NAIL ENAMEL COMPOSITIONS HAVING DECORATIVE APPEARANCE

[75] Inventors: Robert L. Socci, Cedar Grove, N.J.; Anatoly Ismailer, Roslyn Heights, N.Y.

[73] Assignee: Kirker Enterprises, Inc., Paterson, N.J.

[21] Appl. No.: 09/327,799

[22] Filed: Jun. 8, 1999

Related U.S. Application Data

[60] Provisional application No. 60/088,520, Jun. 8, 1998.

[51] Int. Cl.⁷ .............................. A61K 7/04; A61K 7/00; A61K 9/00
[52] U.S. Cl. ........................ 424/61; 424/400; 424/401
[58] Field of Search .................... 424/400, 401, 424/61

[56] References Cited

U.S. PATENT DOCUMENTS

| | | |
|---|---|---|
| Re. 16,760 | 10/1927 | Egelhoff . |
| 1,689,892 | 10/1928 | Root . |
| 1,732,661 | 10/1929 | Root . |
| 2,021,152 | 11/1935 | Neuhaus . |
| 2,248,254 | 7/1941 | Small . |
| 2,350,818 | 6/1944 | Rees . |
| 2,576,290 | 11/1951 | Fisher, Jr. ................... 117/41 |
| 2,612,456 | 9/1952 | Thacker et al. ............ 117/41 |
| 2,714,560 | 8/1955 | Hookway ................... 117/41 |
| 2,763,568 | 9/1956 | McBride ................... 117/41 |
| 3,506,474 | 4/1970 | Neuhaus et al. ............ 117/41 |
| 3,769,063 | 10/1973 | Kizawa ...................... 117/41 |
| 3,829,323 | 8/1974 | Kirch ........................ 117/45 |
| 4,158,053 | 6/1979 | Greene et al. ............. 424/61 |
| 4,166,054 | 8/1979 | Meeske et al. ........... 260/23 |
| 4,812,336 | 3/1989 | Okamoto et al. ......... 427/257 |
| 5,266,322 | 11/1993 | Myers et al. ............. 424/401 |
| 5,601,876 | 2/1997 | Oates et al. .............. 427/257 |
| 5,792,447 | 8/1998 | Socci et al. ............... 424/61 |
| 5,817,304 | 10/1998 | Mondet et al. .......... 424/78.03 |
| 5,863,523 | 1/1999 | Socci et al. ............... 424/61 |
| 5,935,590 | 8/1999 | Razzano .................. 424/401 |
| 5,989,575 | 11/1999 | Razzano .................. 424/401 |

OTHER PUBLICATIONS

Cover Girl Crackle Lacquer Package Insert, Noxell Corp. Distr., 1999.

Textbook of Polymer Science, Fred W. Billmeyer, Jr., 1965, p. 404.

*Primary Examiner*—Shelley A. Dodson
*Assistant Examiner*—Marina Lamm
*Attorney, Agent, or Firm*—Lerner, David, Littenberg, Krumholz & Mentlik, LLP

[57] ABSTRACT

A nail enamel composition of non-toxic components forms a decorative irregular film over natural or synthetic human nails. The nail enamel composition includes an aqueous nail enamel composition of at least one film forming component in an aqueous emulsion or dispersion. The film forming component forms the decorative irregular film containing uniform or random cracks upon drying.

47 Claims, No Drawings

NAIL ENAMEL COMPOSITIONS HAVING DECORATIVE APPEARANCE

The present invention claims the benefit of the U.S. Provisional Application Ser. No. 60/088,520 filed on Jun. 8, 1998, the disclosure of which is incorporated by reference herein.

BACKGROUND OF THE INVENTION

The present invention relates in general to nail enamel compositions, and more particularly, to such compositions which are suitable for coating natural and synthetic nails. Still more particularly, the present invention relates to nail enamel compositions which produce a film having a decorative appearance.

Nail enamel compositions include a class of nail care products regularly used by women as part of their beauty care routine. These nail care products are available in a multitude of product formulations, from clears to infinite colors. Typically, clear nail enamel compositions include a film forming polymer, a film forming resin, a plasticizer and one or more solvents. In the case of a color nail enamel composition, the product may also include a thixotropic compound, a suspending agent and one or more pigments, or in the alternative, an organic coloring polymer may be used. In addition to these components, a number of optional and proprietary components are often included such as UV light absorbers, moisturizers, stabilizers, fragrances and the like.

Nail enamel compositions have heretofore been formulated to satisfy a number of highly desirable film forming properties. For example, desirable properties often include smoothness of application, rapid dry time, scratch resistance, detergent and oil resistance, lustrous appearance, wear and chip resistance and the like. Often most important, it has been highly desirable that the resulting nail enamel film be smooth and uninterrupted by imperfections, for example, orange peel effect, wrinkling, cracking, pitting, bubbling and the like. To this end, nail enamel compositions have included many different types of additives in order to improve the aforementioned desirable properties of the resulting film.

Despite the improved properties of the nail enamel film, the aesthetic or decorative appearance differed very little, except generally for color. Often, manufacturers would produce nail enamel compositions having the same popular colors as their competitors. This provided little distinction between nail enamel products of different manufacturers to the ultimate consumer. Nail enamel compositions having a more decorative appearance were produced by including small pieces of light reflecting decorative material known as glitters within the composition. From the foregoing, it can be appreciated that the appearance of nail enamel compositions have differed very little over the years. To this end, the present invention provides a nail enamel composition which produces a film having a textured decorative appearance heretofore unknown.

Paints and lacquers for furniture and home remodeling applications having an irregular film, for example, a wrinkle or crackle finish have been known for many years. For example, paints and lacquers having a crackle finish are known from Egelhoff, U.S. Pat. No. Re. 16,760; Neuhaus, U.S. Pat. No. 2,021,152; Rees, U.S. Pat. No. 2,350,818; Thacker, et al., U.S. Pat. No. 2,612,456; Hookway, U.S. Pat. No. 2,714,560; and Oates, et al., U.S. Pat. No. 5,601,876. Paints and lacquers having a wrinkle finish are known from Root, U.S. Pat. Nos. 1,689,892 and 1,732,661; Small, U.S. Pat. No. 2,248,254; Ficher, U.S. Pat. No. 2,576,290; McBride, U.S. Pat. No. 2,763,568; Neuhaus, et al., U.S. Pat. No. 3,506,474; Kirch, U.S. Pat. No. 3,829,323; and Okamoto, et al., U.S. Pat. No. 4,812,336. These known paints and lacquers are not suitable for human contact due to the inclusion of generally toxic compounds and those which are not approved by the FDA.

Despite these known paints and lacquers, there has heretofore been unknown nail enamel compositions containing non-toxic components which when applied to natural or synthetic nails will produce a film having a textured decorative appearance.

SUMMARY OF THE INVENTION

In accordance with one embodiment of the present invention there is described a nail enamel composition of non-toxic components for forming an irregular film over natural or synthetic human nails, the composition comprising an aqueous nail enamel composition including at least one film forming component in an aqueous emulsion or dispersion, the film forming component forming an irregular film upon drying.

In accordance with another embodiment of the present invention there is described a nail enamel kit of non-toxic components for forming an irregular film over natural or synthetic human nails, the kit comprising a base nail enamel composition including at least one base coat film forming component, the base coat film forming component forming a film over the natural or synthetic nails, and an aqueous nail enamel composition including at least one top coat film forming component in an aqueous emulsion or dispersion, the top coat film forming component forming an irregular film upon drying over the film formed from the base coat film forming component.

In accordance with another embodiment of the present invention there is described a method of forming an irregular film over natural or synthetic human nails, the method comprising applying an aqueous nail enamel composition of non-toxic components including at least one top coat film forming component in an aqueous emulsion or dispersion over the natural or synthetic nails, the top coat film forming component forming an irregular film upon drying.

DETAILED DESCRIPTION OF THE PREFERRED EMBODIMENTS

In describing the preferred embodiments of the subject matter to be described, specific terminology will be resorted to for the sake of clarity. However, the invention is not intended to be limited to the specific terms so selected, and is to be understood that each specific term includes all technical equivalence which operate in a similar manner to accomplish a similar purpose.

The present invention broadly discloses nail enamel compositions which, when forming a film therefrom, will exhibit a decorative appearance by virtue of forming an irregular film. By irregular film, it is meant that the film will contain a plurality of cracks in either a uniform or random pattern. The term crack is intended to have its ordinary meaning. For example, a crack is a fissure or complete or partial split, break or fine lines in the nail enamel film so as to produce, for example, slight or narrow spaces or voids. A pseudocrack is also contemplated wherein a thinning of the nail enamel film occurs to produce the appearance of a crack. The cracks may be of uniform or random patterns formed over the natural or synthetic nail which are produced during drying of the nail enamel composition.

The nail enamel compositions of the present invention which produce an irregular film are applied to natural or synthetic nails which have been previously coated with a base nail enamel composition. It is contemplated that four operative nail enamel coating systems can be produced for creating an irregular film in accordance with the present invention. These systems are classified as to whether the nail enamel composition is based upon an organic solvent or an aqueous medium for forming an emulsion or dispersion such as a colloidal dispersion of the film forming components. Specifically, the four systems include (1) a solvent base coat composition for receiving a solvent top coat composition which forms an irregular film, (2) an aqueous base coat composition for receiving an aqueous top coat composition which forms an irregular film, (3) a solvent base coat composition for receiving an aqueous top coat composition which forms an irregular film and (4) an aqueous base coat composition for receiving a solvent top coat composition which forms an irregular film. For purposes of the present application, a base nail enamel composition or base composition will refer to the composition which is applied directly to the natural or synthetic nail. On the other hand, a decorative nail enamel composition or decorative composition refers to the nail enamel composition which forms the irregular film having cracks pursuant to the present invention.

Solvent base coat compositions can be formulated as a clear or color nail enamel composition which is suitable for coating natural and synthetic nails. Typically, a clear nail enamel composition contains one or more film forming components, a plasticizer and one or more solvents. In the case of a color base coat nail enamel composition, the composition will generally include a thixotropic compound, a suspending agent and one or more pigments, or in the alternative, an organic coloring polymer may be used. In addition to these compounds, a number of optionally and proprietary components may be included such as UV light absorbers, moisturizers, stabilizers, fragrances and the like. Suitable solvent base coat nail enamel compositions are disclosed in U.S. patent application Ser. No. 09/056,111, entitled Quick Drying Nail Enamel Composition, filed on Apr. 7, 1998 in the name of Socci, et al.; U.S. Pat. No. 5,863,523, entitled Nail Enamel Composition, filed on Dec. 10, 1996 in the name of Socci, et al.; and U.S. Pat. No. 5,792,447, entitled Nail Enamel Composition, filed on Nov. 15, 1996 in the name of Socci, et al., which application and patents are assigned to the same assignee of the present application, the disclosures of which are incorporated herein by reference.

The solvent base coat nail enamel compositions may contain one or more film forming components such as film forming polymers, for example, cellulose acetate, cellulose acetate butyrate, ethyl cellulose, vinyl polymers, nitrocellulose, as well as methacrylate and acrylate type polymers, and mixtures thereof. Nitrocellulose provides an unusual combination of properties of toughness, durability, solubility and solvent release. Examples of nitrocellulose are the so called nitrocellulose RS ⅛ sec. and ¼ sec.; nitrocellulose RS ½ sec.; and nitrocellulose RS 5–6 sec. and 60–80 sec., which have higher viscosities than the earlier grades. The term "RS" refers to the brand of nitrocellulose with a nitrogen content of about 11.2–12.8% with solubility in esters, ketones and glycol ethers manufactured by Hercules, Inc. The terms ⅛ sec., ¼ sec., ½ sec., 5–6 sec., etc. represent viscosity and refer to the time it takes for a ball to fall to a given depth in the material. Nitrocellulose is typically supplied in 70% concentrations, wet with 30% ethyl or isopropyl alcohol. As used in the present application, the percentage of nitrocellulose in a given composition will be on a wet basis unless otherwise stated. Nail enamel compositions of the present invention may include the above film forming polymers and combinations thereof in an amount ranging from about 5 to 25% by weight, and more preferably in the range of about 10 to 15% by weight.

In addition to the aforementioned film forming polymers, the solvent base coat nail enamel compositions can also include one or more film forming resins. Exemplary film forming resins which may be used in the present invention either alone or in combination with the film forming polymers include, for example, drying and non-drying alkyd resins, polyvinyl resins for example polyvinyl acetate, polyester resins, epoxy resins, acrylic polymers and copolymers, maleic modified glycerol esters of rosin, and toluene sulfonamide/epoxy resins, e.g., tosylamide epoxy resin. It is also within the scope of the solvent base coat compositions of the present invention to include aldehyde condensation products such as arylsulfonamide formaldehyde resins, specifically toluene sulfonamide formaldehyde resin which is a condensation product of formaldehyde and toluene sulfonamide. The amount of film forming resin and combinations thereof can range from about 2 to 25% by weight of the composition, and preferably about 7 to 12% by weight of the composition. Overall, the solvent base coat nail enamel composition can include a number of film forming components in the overall range of from about 2 to 25% by weight of the composition, and preferably about 10 to 15% by weight of the composition.

In addition to the film forming components, the solvent base coat nail enamel compositions according to the present invention will generally include at least one plasticizer to soften and plasticize particularly the film forming polymer. The plasticizer may be in either liquid or solid form, as well as combinations thereof. The solvent base coat compositions may include one or more of the known plasticizers which are suitable for use in nail enamel compositions. Examples of such known plasticizers include tricresyl phosphate, dibutyl tartrate, benzyl benzoate, tributyl phosphate, butyl acetyl ricinoleate, butyl glycolate, butyl stearate, triphenyl phosphate, triethyl citrate, camphor, castor oil, esters of citric, stearate, phalic, oleic, phosphate, butyric and benzoic acid, glyceryl triacetate and glyceryl triproprionate, 2,2,4-trimethyl-1,3-pentandiiol diisobutyrate and mixtures thereof. The solvent base coat nail enamel compositions of the present invention also contemplate the use of phthalate type plasticizers either alone or in combination with the aforementioned plasticizers, for example, diamylphthalate, dibutyl phthalate, diethyl phthalate, dioctyl phthalate, dibutoxy ethylphthalate and mixtures thereof.

Plasticizers included in the solvent base coat compositions of the present invention are in amounts sufficient to provide acceptable flexibility to the nail enamel film on the human or synthetic nail surface. In this regard, the amount of plasticizer and combinations thereof for use in the solvent base coat compositions of the present invention range from about 1 to 20% by weight, and preferably about 5 to 10% by weight.

The solvent base coat nail enamel compositions of the present invention also include one or more organic solvents such as those generally used in conventional nail enamel compositions. Examples of these solvents include ethyl acetate, methyl acetate, ethanol, isopropanol, propyl acetate, n-butanol, xylene, DI acetone alcohol, aromatic (containing phenyl groups), amyl acetate, ethers, ketones, alkanes for example, pentane, cyclopentane, hexane, toluene, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, chlorinated hydrocarbons for example, methylene chloride, chloroform and methylchloroform. The aforementioned solvents can be used alone or in mixtures thereof. In general, the amount of solvent used in the compositions of the present invention range from about 60 to 80% by weight, and preferably about 65 to 75% by weight.

In color solvent base coat compositions according to the present invention, one or more pigments and a suspending agent may also be added. One or more known organic colorants which are well known in the nail enamel art may also be added to these compositions. Pigments are added to the composition to provide cosmetically acceptable shades and to pacify the films. Pigments for use in the present invention may include any of those pigments which are generally known for use in nail enamel compositions. For example, these pigments can include cosmetic grade or purified titanium dioxide, yellow and red iron oxides, bismuth oxychloride, iron blue, iron black, mica particles, ultramarine blue, D&C Red #7, chromide oxide greens, carbon black, lampblack and the like. Other pigments which may be used in compositions according to the present invention may include the Lake pigments, for example, D&C Red #6 barium Lake, D&C Red #7 calcium Lake and the like.

In addition to the above named pigments, there may also be included titanated micas, polyethylene teraphthalates and pearl essence which is a suspension of crystalline guanine in nitrocellulose and solvents, as well as other additives which will affect the appearance of the pigment. Although the amount of pigment in the compositions of the present invention will vary as a function of the type of pigment and other components included in the composition, in general, pigments can be included in an amount up to about 10% by weight of the nail enamel composition.

When pigments are included in compositions according to the present invention, it is useful to include a suspending agent for enhancing the suspension of the pigments in the other components of the solvent base coat composition. Although a number of suspending agents which are generally used in conventional nail enamel compositions may be used to produce compositions according to the present invention, preferred suspending agents include colloidal clays, montmorillonite clays, especially stearalkonium hectorite, stearalkonium bentonite, fumed silica, and mixtures thereof. The suspending agent is present in the compositions of the present invention in amounts sufficient to produce a gel, preferably a colloidal gel. In general, the suspending agent is included in the amount ranging from about 0.5 to 5% by weight of the solvent base coat nail enamel composition.

In addition to the above described components, the solvent base coat compositions of the present invention may also include additional additives including stabilizers, thixotropic agents, light absorbers such as ectocrylene and benzophenone-1, fragrances, moisturizers and medicants, depending on the intended result. These components are well known in the art and may be included in amounts well within the teachings of the prior art.

The solvent base coat nail enamel compositions in accordance with the present invention can be manufactured by thoroughly and intimately mixing together all the components in the amounts described in accordance with the present invention. Examples of satisfactory equipment and how to use then are readily apparent to one of ordinary skill in the nail enamel art.

The following examples illustrate solvent base coat nail enamel compositions of the present invention. These examples are by way of illustration and are not intended to be limiting the present invention either as to the inclusion of a lesser number of components, the substitution of additional components or variations in the percentages of the range of components.

| EXAMPLE 1 | |
|---|---|
| | WT/PERCENT |
| ETHYL ACETATE | 43.60 |
| BUTYL ACETATE | 12.40 |
| NITROCELLULOSE | 12.00 |
| ISOPROPYL ALCOHOL | 5.50 |
| TOSYLAMIDE EPOXY RESIN | 6.50 |
| SUCROSE ACETATE ISOBUTYRATE | 5.00 |
| R779 ACRYLATES COPOLYMER | 3.75 |
| TRIPHENYL PHOSPHATE | 3.75 |
| POLYESTER RESIN | 0.75 |
| DIBUTYL PHTHALATE | 0.50 |
| DIACETONE ALCOHOL | 0.50 |
| BENZOPHENONE 1 | 0.10 |
| POLYETHER MODIFIED DIMETHYLPOLYSILOXANE | 0.50 |
| DIMETHICONE | 0.20 |
| STEARALKONIUM HECTORITE | 1.00 |
| TITANIUM DIOXIDE | 1.00 |
| D&C RED #6 CALCIUM LAKE | .75 |
| RED IRON OXIDE | 1.00 |
| BLACK IRON OXIDE | .20 |
| MICA | 1.00 |

| EXAMPLE 2 | |
|---|---|
| | WT/PERCENT |
| ETHYL ACETATE | 37.01 |
| BUTYL ACETATE | 14.20 |
| NITROCELLULOSE | 12.80 |
| ISOPROPYL ALCOHOL | 6.40 |
| TOSYLAMIDE EPOXY RESIN | 6.60 |
| SUCROSE ACETATE ISOBUTYRATE | 5.90 |
| ACRYLATES COPOLYMER | 0.70 |
| TRIPHENYL PHOSPHATE | 2.70 |
| POLYESTER RESIN | 1.20 |
| DIBUTYL PHTHALATE | 0.90 |
| CAMPHOR | 0.10 |
| HEPTANE | 0.30 |
| PROPYL ACETATE | 0.20 |
| STEARALKONIUM HECTORITE | 0.10 |
| STEARALKONIUM BENTONITE | 1.10 |
| DIACETONE ALCOHOL | 0.70 |
| BENZOPHENONE 1 | 0.30 |
| POLYETHER MODIFIED DIMETHYLPOLYSILOXANE | 0.40 |
| ETOCRYLENE | 0.05 |
| DIMETHICONE | 0.10 |
| TITANIUM DIOXIDE | 0.20 |
| FD&C YELLOW #5 ALUMINUM LAKE | 1.00 |
| FERRIC AMMONIUM FERROCYANIDE | 0.04 |
| MICA | 7.00 |

EXAMPLE 3

| | WT/PERCENT |
|---|---|
| ETHYL ACETATE | 41.20 |
| BUTYL ACETATE | 15.80 |
| NITROCELLULOSE | 11.50 |
| ISOPROPYL ALCOHOL | 6.40 |
| TOSYLAMIDE EPOXY RESIN | 6.60 |
| SUCROSE ACETATE ISOBUTYRATE | 5.90 |
| ACRYLATES COPOLYMER | 0.70 |
| TRIPHENYL PHOSPHATE | 2.90 |
| POLYESTER RESIN | 0.60 |
| DIBUTYL PHTHALATE | 1.70 |
| CAMPHOR | 0.20 |
| HEPTANE | 0.50 |
| PROPYL ACETATE | 0.50 |
| STEARALKONIUM HECTORITE | 0.10 |
| STEARALKONIUM BENTONITE | 0.80 |
| DIACETONE ALCOHOL | 0.50 |
| BENZOPHENONE 1 | 0.05 |
| POLYETHER MODIFIED DIMETHYL POLYSILOXANE | 0.40 |
| ETOCRYLENE | 0.05 |
| DIMETHICONE | 0.10 |
| TITANIUM DIOXIDE | 2.00 |
| FD&C YELLOW #5 ALUMINUM LAKE | 0.10 |
| RED IRON OXIDE | 0.10 |
| BLACK IRON OXIDE | 1.30 |

EXAMPLE 4

| | WT/PERCENT |
|---|---|
| POLYESTER RESIN | 8.40 |
| TOSYLAMIDE EPOXY RESIN | 4.96 |
| NITROCELLULOSE 1/4/5–6 sec. | 8.87 (dry) |
| ETHYL ACETATE | 30.00 |
| BUTYL ACETATE | 27.18 |
| ISOPROPYL ALCOHOL | 11.22 |
| TRIPHENYL PHOSPHATE | 4.62 |
| 2,2,4-TRIMETHYL-1,3-PENTANEDIOL DIISOBUTYRATE | .85 |
| DIBUTYL PHTHALATE | .50 |
| CAMPHOR | .10 |
| DIACETONE ALCOHOL | .68 |
| CITRIC ACID | 0.02 |
| STEARALKONIUM HECTORITE | .25 |
| STEARALKONIUM BENTONITE | .78 |
| D & C RED #6 BARIUM LAKE | .90 |
| D & C RED #7 CALCIUM LAKE | .35 |
| TITANIUM DIOXIDE | .32 |

EXAMPLE 5

| | WT/PERCENT |
|---|---|
| NITROCELLULOSE 1/4/1/2 sec. | 12.52 (dry) |
| TOLUENE SULFONAMIDE FORMALDEHYDE RESIN | 8.12 |
| BUTYL ACETATE | 22.79 |
| ETHYL ACETATE | 18.74 |
| TOLUENE | 19.69 |
| ISOPROPYL ALCOHOL | 5.72 |
| CAMPHOR | 1.10 |
| BENZOPHENONE 1 | 0.04 |
| DIBUTYL PHTHALATE | 5.92 |
| DIACETONE ALCOHOL | .84 |
| STEARALKONIUM HECTORITE | .05 |
| STEARALKONIUM BENTONITE | 1.24 |

-continued

EXAMPLE 5

| | WT/PERCENT |
|---|---|
| CITRIC ACID | 0.02 |
| POLYESTER RESIN | 1.07 |
| TOLUENE SULFONAMIDE EPOXY | 0.15 |
| TITANIUM DIOXIDE | .33 |
| D & C RED #6 BARIUM LAKE | .90 |
| D & C RED #7 CALCIUM LAKE | .76 |

EXAMPLE 6

| | WT/PERCENT |
|---|---|
| POLYESTER RESIN | 5.60 |
| TOSYLAMIDE EPOXY RESIN | 4.95 |
| NITROCELLULOSE 1/4/5–6 sec. | 8.85 (dry) |
| ETHYL ACETATE | 32.50 |
| BUTYL ACETATE | 26.50 |
| ISOPROPYL ALCOHOL | 11.50 |
| TRIPHENYL PHOSPHATE | 4.65 |
| 2,2,4-TRIMETHYL-1,3-PENTANEDIOL DIISOBUTYRATE | .92 |
| DIBUTYL PHTHALATE | .50 |
| CAMPHOR | .10 |
| DIACETONE ALCOHOL | .68 |
| CITRIC ACID | 0.02 |
| STEARALKONIUM HECTORITE | .25 |
| STEARALKONIUM BENTONITE | .75 |
| TITANIUM DIOXIDE | 1.16 |
| IRON OXIDES | .27 |
| D & C RED #7 | .20 |
| ETOCRYLENE | .50 |
| MICA | .10 |

EXAMPLE 7

| | WT/PERCENT |
|---|---|
| NITROCELLULOSE 1/4/1/2 sec. | 12.57 (dry) |
| POLYESTER RESIN | 8.10 |
| TOLUENSULFONAMIDE EPOXY RESIN | .35 |
| ETHYL ACETATE | 30.39 |
| BUTYL ACETATE | 16.75 |
| BUTYL ALCOHOL | 1.71 |
| PROPYL ACETATE | 9.44 |
| ISOPROPYL ALCOHOL | 9.74 |
| DIBUTYL PHTHALATE | 6.19 |
| CAMPHOR | 1.10 |
| DIACETONE ALCOHOL | .66 |
| STEARALKONIUM BENTONITE | 1.01 |
| STEARALKONIUM HECTORITE | .02 |
| ETOCRYLENE | .50 |
| BENZOPHENONE 1 | 0.08 |
| CITRIC ACID | 0.02 |
| TITANATED MICA | 0.12 |
| TITANIUM DIOXIDE | 1.00 |
| D & C RED #6 BARIUM LAKE | .05 |
| IRON OXIDES | .10 |
| D & C RED #7 CALCIUM LAKE | .10 |

Aqueous base coat nail enamel compositions contain one or more aqueous emulsion or dispersion polymers which include copolymers which are suitable for forming an adherent film to a natural or synthetic nail. By way of example, these aqueous polymers include the general class of acrylic polymers, such as styrenated acrylic polymers capable of forming colloidal dispersions and emulsions, polyurethane and polyurethane copolymers, vinyl acetate polymers and copolymers, olefin polymers and copolymers, those noted hereinafter with respect to the aqueous decorative nail enamel compositions and the like. Other suitable aqueous polymers are disclosed in Myers, et al., U.S. Pat. No. 5,266,322 which discloses a first aqueous emulsion containing a sulfopolyester and a copolymer of vinyl acetate and dialkyl maleate and a second aqueous emulsion which contains acetoacetoxy-ethyl alkylacrylate, or the reaction product of acetoacetoxy-ethyl alkylacrylate with a vinyl functional monomer; and Green, et al., U.S. Pat. No. 4,158,053 which discloses aqueous emulsion copolymers having a solid content of from about 30–55% and a glass transition temperature within the range of about −10–50° C., which is prepared by the polymerization of two or more specific types of disclosed monomers. The polymers and copolymers disclosed in Myers, et al. and Green, et al. are incorporated herein by reference.

By way of example, styrenated acrylic emulsion polymers suitable for use in an aqueous base coat nail enamel composition are obtainable from S.C. Johnson Polymer, a division of S.C. Johnson Commercial Markets, Inc. of Sturtebant, Wis. under the marks Joncryl 1907, Joncryl 1908 and Joncryl 2561. Joncryl 1907 is supplied as an emulsion containing 46% non volatiles by weight, a viscosity of 500 cps with a glass transition temperature Tg of 21° C. Joncryl 1908 is supplied as an emulsion containing 48% by weight non volatiles having a viscosity of 500 cps and a glass transition temperature Tg of 95° C. and Joncryl 2561 is supplied as an emulsion containing 48% by weight non volatiles having a viscosity of 700 cps and a glass transition temperature Tg of −11° C. The aqueous base coat nail enamel composition of the present invention may include aqueous polymers and copolymers, based on an emulsion or dispersion and combinations thereof in an amount ranging up to 100% of the composition.

In addition to the aforementioned aqueous polymers, the aqueous base coat nail enamel compositions can include one or more coalescing solvents which facilitates the aqueous polymer to form a continuous polymer film. Exemplary coalescing solvents which may be used in the present invention either alone or in combination include, for example, glycol ethers, such as ethylene glycol monobutyl ether, diethylene glycol monomethyl ether, propylene glycol monomethyl ether, dipropylene glycol monomethyl ether, isopropyl alcohol, butyl carbitol, ethylene glycol 2-ethyl hexyl ether, ethylene glycol phenyl ether, diethylene glycol monopropyl ether, diethylene glycol monohexyl ether, diethylene glycol monobutyl, propylene glycol monopropyl ether, propylene glycol tertiary butyl ether, dipropylene glycol monopropyl ether, dipropylene glycol tertiary butyl ether, dipropylene glycol monobutyl ether, tripropylene glycol methyl ether, aromatic based glycol ether, 2,2,4-trimethyl-1,3-pentanediol monoisobutyrate, benzyl alcohol, n-methyl pyrolidone, diacetone alcohol, exxate 700, exxate 800, exxate 900, exxate 1000, exxate 1300 and mixtures thereof. The aqueous base coat compositions of the present invention may include coalescing solvents and combinations thereof in an amount ranging from about 1 to 20% by weight, and more preferably, in the range of about 5 to 10% by weight of the composition.

The aqueous base coat compositions of the present invention may also include additional additives, including colorants such as pigments and organic colorants such as tints and dyes, dispersing agents, wetting agents, thickeners, suspending agents, anti-foams, buffers, chelating agents, anti-freezing agents, UV light absorbing agents, stabilizers, fillers, etc. The selection of these optional ingredients is well within the skill of those familiar with the nail enamel art.

By way of example only, any of the aforementioned pigments or organic colorants may be used in an aqueous base coat nail enamel composition to impart color if desired. Suitable pigments by way of one example only are available as an aqueous dispersion containing styrene acrylic resin from Sun Chemical Corporation of Cincinnati, Ohio. Organic colors referred to as tints are available from Penn Color of Doylestown, Pa. In addition, suspending agents as noted herein may be used to prevent separation and settling of pigmented aqueous base coat compositions.

The aqueous base coat nail enamel compositions in accordance with the present invention can be manufactured in a similar manner as previously noted by thoroughly and intermittently mixing together all of the components in the amounts described in accordance with the present invention. The following examples are provided to illustrate suitable aqueous base coat compositions which are capable of forming a continuous film at room temperature. These examples are by way of illustration and are not intended to be limiting the present invention either as to the inclusion of a lesser number of components, the substitution of additional components or variations in the percentages of the range of components.

|  | WT/PERCENT |
|---|---|
| JONCRYL 1908 | 67.00 |
| JONCRYL 1907 | 20.00 |
| ISOPROPYL ALCOHOL | 3.50 |
| TERTIARY BUTYL ETHER PROPYLENE GLYCOL | 3.00 |
| DIBUTYL PHTHALATE | 3.50 |
| WATER | 3.00 |

|  | WT/PERCENT |
|---|---|
| JONCRYL 1907 | 91.00 |
| ISOPROPYL ALCOHOL | 6.50 |
| DIBUTYL PHTHALATE | 2.50 |

|  | WT/PERCENT |
|---|---|
| COMPOSITION OF EXAMPLE 8 | 97.08 |
| PIGMENT DISPERSIONS: WATER/STYRENE-ACRYLIC RESIN | 2.92 |

|  | WT/PERCENT |
|---|---|
| JONCRYL 1907 | 90.00 |
| TERTIARY BUTYL ETHER PROPYLENE GLYCOL | 4.2 |
| ISOPROPYL ALCOHOL | 2.5 |
| PENN COLOR SOLUTION 365282 | 3.3 |

|  | WT/PERCENT |
| --- | --- |
| JONCRYL SCX-1970 | 90.00 |
| ISOPROPYL ALCOHOL | 2.5 |
| BUTYL CELLOSOLVE | 5.0 |
| PENN COLOR SOLUTION 365282 | 3.5 |

A solvent decorative nail enamel composition in accordance with the present invention which evidences cracking upon drying can be formulated for application over either a solvent or aqueous base nail enamel composition of the types previously described. In formulating solvent decorative compositions, the composition generally contains a low percentage of film forming components, i.e., binders, and a high percentage of inert material as fillers. Suitable inert material include, for example, pigments, talc, hydrated silica, zinc stearate, colloidal clays, micas, bismuth oxychloride, fumed silica and the like, as well as mixtures thereof. Any suitable inert material which will provide the solvent decorative composition with a high percentage of solids are contemplated as suitable for use in accordance with the present invention. Solvent decorative nail enamel compositions of the present invention may include inert material in an amount ranging from about 5 to 70% by weight, and more preferably in the range of about 30 to 40% by weight of composition. It is to be noted that the pigments can be selected to provide the desired color to the resulting film which may also include organic colorants.

In order to provide an adherent film from the film forming components, the amount of inert material present should generally be less than the critical pigment volume concentration. This concentration is defined as the level of inert material where the film forming component just surrounds each pigment particle without the pigments touching one another. In the event there is insufficient amount of film forming components, the pigments will touch each other which will provide a brittle or non-cohesive film, i.e., the concentration of inert material being greater than the critical pigment volume concentration. It is to be noted that the critical pigment volume concentration will vary from pigment to pigment and from binder to binder. The specific critical pigment binder concentration for any particular pigment/binder system can be obtained by trial and error and is considered within the knowledge of those skilled in the nail enamel art.

The solvent decorative nail enamel composition includes a relatively low percentage of film forming component which functions as a binder for the pigments or inert material. Any of the aforementioned solvent film forming components, for example, nitrocellulose, cellulose acetate butylate and the like may be used in the composition. The solvent decorative compositions of the present invention may include the film forming components and combinations thereof in an amount ranging from about 5 to 25% by weight, and more preferably, in the range of about 5 to 10% by weight of the composition.

In addition to the above described components, the solvent decorative nail enamel compositions of the present invention will also include one or more of the aforementioned solvents which may be present in the range of about 30 to 90% by weight, and preferably, about 60 to 75% by weight of the composition. Additional components may include one or more of the above-mentioned plasticizers, suspending agents, stabilizers, UV light absorbers, fragrances, moisturizers, medicants, etc., depending upon the intended result.

The following examples of solvent decorative nail enamel compositions in accordance with the present invention are presented by way of illustration only. These examples are by way of illustration and are not intended to be limiting the present invention either as to the inclusion of a lesser number of components, the substitution of additional components or variations in the percentages of the range of components.

|  | WT/PERCENT |
| --- | --- |
| NITROCELLULOSE 1/4 sec. | 2.50(dry) |
| FUMED SILICA | 7.60 |
| BUTYL ACETATE | 30.00 |
| ETHYL ACETATE | 42.60 |
| ETHANOL | 16.20 |
| ISOPROPYL ALCOHOL | 1.10 |

|  | WT/PERCENT |
| --- | --- |
| COMPOSITION OF EXAMPLE 14 | 85.71 |
| WHITE PIGMENT | 14.29 |

|  | WT/PERCENT |
| --- | --- |
| PASTE COMPOSITION: | |
| ETHYL ACETATE | 75.00 |
| NITROCELLULOSE 1/4 sec. | 5.00 (dry) |
| HYDRATED SILICA | 20.00 |
| SOLVENT DECORATIVE COMPOSITION: | |
| PASTE COMPOSITION OF EXAMPLE 16 | 30 parts |
| COMMERCIAL TOLUENE FORMALDEHYDE FREE NAIL ENAMEL #Ver 1033 | 15 parts |

|  | WT/PERCENT |
| --- | --- |
| NITROCELLULOSE 1/4 sec. | 2.50 (dry) |
| TITANIUM DIOXIDE | 40.00 |
| BUTYL ACETATE | 20.00 |
| ETHYL ACETATE | 34.40 |
| ETHANOL | 4.00 |
| ISOPROPYL ALCOHOL | 1.10 |

Aqueous decorative nail enamel compositions may include one or more of the aforementioned aqueous polymers and copolymers which may be in the form of either an aqueous emulsion or dispersion, such as a colloidal dispersion. In particular, by way of example only, suitable aqueous polymers include those referred to as acrylic polymers, styrenated acrylic polymers, acrylic-urethane polymers, vinyl acrylates, in addition to those mentioned hereinabove with respect to the aqueous base coat nail enamel compositions, and mixtures thereof. In selecting a suitable aqueous polymer, one criteria is the polymer's glass transition temperature, $T_g$,° C. By glass transition temperature it is meant the temperature at which the non-crystalline portion of the polymer is transformed from a generally tough, rubbery material to a generally brittle, glass-like material. It is contemplated that suitable aqueous polymers having a glass transition temperature in the range of from about 0°

C.–95° C. or greater will be suitable for use in the aqueous based decorative nail enamel compositions of the present invention. Generally, any aqueous polymer having a glass transition temperature greater than 0° C. is considered to be acceptable, the desirable range being a glass transition temperature of higher than 10° C., and most preferably a glass transition temperature of about 95° C.

Suitable aqueous polymers for the aqueous decorative nail enamel compositions of the present invention specifically include those previously designated as Joncryl 1907 and Joncryl 1908. Additional aqueous acrylic emulsion polymers which are suitable are known as Joncryl 530 which is an emulsion polymer having 49% by weight non-volatiles and a glass transition temperature of 75%° C., Joncryl 95 which is a colloidal polymer dispersion having a non-volatile content of 30% by weight and a glass transition temperature of 43° C., Joncryl SCX-1532 which is an emulsion polymer having 51% by weight non-volatiles and a glass transition temperature of 12° C., Joncryl SCX-2500 which is an emulsion polymer having 43% by weight non-volatiles and a glass transition temperature of 13° C., Joncryl 538 which is an emulsion polymer having 45% by weight non-volatiles and a glass transition temperature of 64° C. and Joncryl SCX 1970 which is an emulsion polymer having 48% by weight non-volatiles and a glass transition temperature of 78° C., the aforementioned aqueous polymers being available from S.E. Johnson Polymer. In addition, aliphatic waterborne urethane polymers such as Sancure 1073C which is available from B.F. Goodrich Specialty Chemicals of Cleveland, Ohio is also suitable for use in an aqueous decorative nail enamel composition. Sancure 1073C has a 30% non-volatiles content at a sward hardness of 100. From the foregoing, it should be appreciated that a large number of aqueous emulsion and colloidal dispersion polymers and copolymers having glass transition temperatures greater than 0° C. are suitable for use in an aqueous decorative nail enamel composition in accordance with the present invention.

It is contemplated that, by way of theory only, and not to be bound thereby, that the higher the glass transition temperature, the faster and greater the severity of cracking will occur in the aqueous decorative nail enamel composition. In this regard, the higher the glass transition temperature, the more brittle the resulting film and the greater degree and severity of cracking to be expected. Accordingly, glass transition temperatures of about 95° C. and above have been found to be most preferred for forming an aqueous decorative nail enamel composition pursuant to the present invention, although a glass transition temperature in the range of about 0 to 95° C. and greater is also contemplated in accordance with the present invention. The aqueous nail enamel compositions of the present invention may include aqueous emulsion and dispersion polymers and copolymers, and combinations thereof, in varying amounts up to 100% of the composition.

It is also contemplated that suitable aqueous decorative nail enamel compositions pursuant to the present invention can include the aforementioned aqueous dispersion and colloidal polymers and copolymers without additional additives. That is, it is contemplated that the aqueous decorative compositions may comprise an aqueous emulsion or colloidal dispersion of the aforementioned polymers and copolymers having a suitable glass transition temperature to provide an irregular film upon application over an aqueous or solvent base coat nail enamel composition.

In addition to controlling the glass transition temperature, varying degrees in the textured decorative appearance, e.g., degree or severity of cracking of the irregular film formed from an aqueous decorative nail enamel composition can be affected by the presence of a coalescing solvent and/or plasticizer. In this regard, it is contemplated that the use of coalescing solvents and/or plasticizers will lower the glass transition temperature of the aqueous emulsion or dispersion polymers and copolymers rendering them less brittle so as to facilitate the formation of a film with varying degrees of cracking. Therefore, it is contemplated that only a small amount of coalescing solvents and/or plasticizers will be used, if desired, to control the decorative appearance of the irregular film being formed from the aqueous nail decorative nail enamel compositions of the present invention.

Coalescing solvents and/or plasticizers are considered more suitable for use in controlling the nature of the irregular film where the polymers and/or copolymers have very high glass transition temperatures subjecting them to being more brittle and less flexible than those of lower glass transition temperatures. Suitable coalescing solvents and plasticizers have been discussed hereinabove, for example, butyl carbitol and dibutyl phthalate.

The aqueous decorative nail enamel compositions of the present invention can also include co-solvents such as isopropyl alcohol, ethyl alcohol, methanol, diacetone alcohol and mixtures thereof. The co-solvents can be used to control the solid content of the composition and the resulting irregular film, as well as increasing the drying rate of the aqueous decorative nail enamel composition when forming an irregular film. Further, the co-solvents will also protect the aqueous decorative compositions against potential freezing during shipping and storage.

As thus far described, the aqueous decorative nail enamel compositions are generally colorless. However, it may be desirable to provide color to the composition. In this regard, any one of well known colorants may be employed. For example, organic and inorganic pigments, as well as organic colorants such as tints or dyes may be used as is well known in the nail enamel art, such as those noted hereinabove. When pigments are employed, a suspending agent such as those previously noted may be employed to assist in the suspension of the pigments. In addition, acrylic copolymer aqueous dispersions may also be used as a suspending agent. One such acrylic copolymer is known as Drewthix 53L which is obtained from Drew Industrial of Boonton, N.J. which is a division of Ashland Chemical Company.

The following examples are provided to illustrate aqueous decorative nail enamel compositions of the present invention. These examples are by way of illustration and are not intended to be limiting the present invention either as to the inclusion of a lesser number of components, the substitution of additional components or variations in the percentages of the range of components. Examples 17–22 provide a colorless aqueous composition, while Examples 23–29 provide an aqueous color nail enamel composition.

|  | WT/PERCENT |
|---|---|
| JONCRYL 1908 | 91.00 |
| ISOPROPYL ALCOHOL | 6.50 |
| DIBUTYL PHTHALATE | 2.50 |

|  | WT/PERCENT |
| --- | --- |
| JONCRYL 530 | 91.50 |
| ISOPROPYL ALCOHOL | 6.50 |
| DIBUTYL PHTHALATE | 2.50 |

|  | WT/PERCENT |
| --- | --- |
| JONCRYL 1908 | 92.00 |
| ISOPROPYL ALCOHOL | 8.00 |

|  | WT/PERCENT |
| --- | --- |
| JONCRYL 530 | 92.00 |
| ISOPROPYL ALCOHOL | 8.00 |

|  | WT/PERCENT |
| --- | --- |
| JONCRYL 1908 | 96.00 |
| BUTYL CARBITOL | 4.00 |

|  | WT/PERCENT |
| --- | --- |
| JONCRYL 530 | 96.00 |
| BUTYL CARBITOL | 4.00 |

|  | WT/PERCENT |
| --- | --- |
| JONCRYL 1908 | 100.00 |
| PENN COLOR SOLUTION 368271 OR 365282 | QS (quotient sufficient) |

|  | WT/PERCENT |
| --- | --- |
| COMPOSITION OF EXAMPLE 17 | 100.00 |
| PENN COLOR SOLUTION 365282 | QS |

|  | WT/PERCENT |
| --- | --- |
| JONCRYL 1908 | 100.00 |
| PENN COLOR SOLUTION 344270 OR SUN CHEMICAL 39–92, 39–95 OR 39–96 | QS |

|  | WT/PERCENT |
| --- | --- |
| TITANIUM DIOXIDE PIGMENT | 38.00 |
| STYRENE ACRYLIC RESIN (JONCRYL) | 7.00 |
| WATER | 55.00 |

|  | WT/PERCENT |
| --- | --- |
| COMPOSITION OF EXAMPLE 26 | 66.23 |
| JONCRYL 1908 | 33.77 |

|  | WT/PERCENT |
| --- | --- |
| JONCRYL 1908 | 27.00 |
| COMPOSITION OF EXAMPLE 26 | 70.60 |
| EASTMAN PM SOLVENT (PROPYLENE GLYCOL MONOMETHYL ETHER) | 2.40 |
| OPTIONAL PIGMENTS AND/OR ORGANIC COLORANTS | QS |

|  | WT/PERCENT |
| --- | --- |
| COMPOSITIONS OF EXAMPLE 26 | 10.00 |
| JONCRYL SCX 1970 | 83.50 |
| EASTMAN PM SOLVENT | 6.00 |
| TAFIGEL PUR-50 (THICKENING AGENT) | 0.50 |

|  | WT/PERCENT |
| --- | --- |
| STYRENE ACRYLIC POLYMER (Tg, 95° C.) | 37.50–41.20 |
| WATER | 37.85–43.00 |
| ISOPROPYL ALCOHOL | 5.60 |
| ETHYL ALCOHOL | 4.80 |
| DIBUTYL PHTHALATE | 3.25 |
| POLYPROPYLENE GLYCOL | 0.85 |
| AMMONIUM HYDROXIDE | 0.85 |
| PIGMENT | 0.25–7.50 |
| QUATERNIUM 15 | 0.17 |
| BENTONITE | 0.01–1.50 |

The aforementioned aqueous or solvent decorative nail enamel compositions produce an irregular film when applied to a natural synthetic nail which has previously been coated with a solvent or aqueous base nail enamel composition. As previously noted, the nail enamel compositions of the present invention which provide an irregular film include four combinations of solvent systems. Specifically, the four systems include (1) a solvent base coat composition for receiving a solvent top coat composition which forms an irregular film, (2) an aqueous base coat composition for receiving an aqueous top coat composition which forms an irregular film, (3) a solvent base coat composition for receiving an aqueous top coat composition which forms an irregular film and (4) an aqueous base coat composition for receiving a solvent top coat composition which forms an irregular film.

Initially, a natural or synthetic nail is coated with either a solvent or aqueous base coat nail enamel composition. The base coat nail enamel composition is preferably allowed to partially dry, for example, to a condition known as "dry to touch." This condition arises when the surface of the resulting film may be touched with one's finger without leaving an impression of one's fingerprints. However, the film has yet to become completely dry. The time period to achieve a dry to touch will depend upon the particular base coat nail enamel composition being used, the thickness of the coat applied, temperature and humidity conditions. Once the base coat nail enamel composition has partially dried, an aqueous or solvent decorative nail enamel composition is applied thereover preferably as a single coat. However, multiple coats may also be applied if so desired. As the decorative nail enamel composition dries, an irregular film will be formed by virtue of the presence of a plurality of uniform or random cracks. These cracks may be small, such as fine hairline cracks, as well as large voids. The cracks or voids allow the color of the underlying base coat composition to show through providing a decorative pattern encompassed by the irregular film.

It is preferred that the base coat nail enamel composition not be completely dry, i.e., only dry to touch. Under these conditions, it is contemplated that the decorative nail enamel composition will strongly adhere to the base coat composition as the compositions completely dry. It has been found that if the base coat composition is initially completely dry, there is the possibility that the decorative nail enamel composition will have poor adherence. However, this condition might not be present when a solvent decorative nail enamel composition is applied over a solvent base coat nail enamel composition. In any event, it is contemplated that a clear protective top coat, either aqueous or solvent based, can be applied to protect the decorative nail enamel composition. The protective top coat may also be tinted if so desired. To this end, there is known from the nail enamel art, as well as the examples disclosed herein, protective clear or tinted top coats which will form a protective continuous film.

Although the invention herein has been described with reference to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

What is claimed is:

1. A nail enamel composition of non-toxic components for forming an irregular film over a base nail enamel composition applied to natural or synthetic human nails, said composition comprising an aqueous nail enamel composition including at least one film forming component having a glass transition temperature greater than about 10° C. in an aqueous emulsion or dispersion, said film forming component forming an irregular film upon drying.

2. The composition of claim 1, wherein said irregular film contains uniform or random cracks therein.

3. The composition of claim 1, wherein said film forming component comprises an aqueous emulsion or colloidal dispersion polymer or copolymer.

4. The composition of claim 3, wherein said film forming component is selected from the group consisting of acrylic polymers, styrenated acrylic polymers, acrylic-urethane polymers, vinyl acrylates, polyurethane, polyurethane copolymers, vinyl acetate polymers and vinyl acetate copolymers, olefin polymers and olefin copolymers.

5. The composition of claim 1, further including a coalescing solvent.

6. The composition of claim 1, further including a plasticizer.

7. The composition of claim 1, further including a pigment or organic colorant.

8. The composition of claim 7, further including a suspending agent.

9. The composition of claim 1, wherein said film forming component has a glass transition temperature greater than about 95° C.

10. A nail enamel kit of non-toxic components for forming an irregular film over natural or synthetic human nails, said kit comprising a base nail enamel composition including at least one base coat film forming component, said base coat film forming component forming a film over said natural or synthetic nails, and an aqueous nail enamel composition including at least one top coat film forming component having a glass transition temperature greater than about 10° C. in an aqueous emulsion or dispersion, said top coat film forming component forming an irregular film upon drying over said film formed from said base coat film forming component.

11. The kit of claim 10, wherein said irregular film contains uniform or random cracks therein.

12. The kit of claim 10, wherein said top coat film forming component comprises an aqueous emulsion or colloidal dispersion polymer or copolymer.

13. The kit of claim 12, wherein said film forming component is selected from the group consisting of acrylic polymers, styrenated acrylic polymers, acrylic-urethane polymers, vinyl acrylates, polyurethane, polyurethane copolymers, vinyl acetate polymers and vinyl acetate copolymers, olefin polymers and olefin copolymers.

14. The kit of claim 10, wherein said aqueous nail enamel composition further includes a coalescing solvent.

15. The kit of claim 10, wherein said aqueous nail enamel composition further includes a plasticizer.

16. The kit of claim 10, wherein said aqueous nail enamel composition further includes a pigment or organic colorant.

17. The kit of claim 10, wherein said top coat film forming component has a glass transition temperature greater than about 95° C.

18. The kit of claim 10, wherein said base coat film forming component comprises a solvent based polymer.

19. The kit of claim 10, wherein said base coat film forming component comprises an aqueous emulsion or colloidal dispersion polymer or copolymer.

20. A method of forming an irregular film over a base nail enamel composition applied to natural or synthetic human nails, said method comprising applying an aqueous nail enamel composition of non-toxic components including at least one top coat film forming component having a glass transition temperature greater than about 10° C. in an aqueous emulsion or dispersion over said base nail enamel composition, said top coat film forming component forming an irregular film upon drying.

21. The method of claim 24, wherein base nail enamel composition of non-toxic components includes at least one base coat film forming component over said natural or synthetic nails, said base coat film forming component forming a film over said natural or synthetic nails.

22. The method of claim 20, wherein said irregular film contains uniform or random cracks therein.

23. The method of claim 20, wherein said top coat film forming component comprises an aqueous emulsion or colloidal dispersion polymer or copolymer.

24. The method of claim 20, wherein said film forming component is selected from the group consisting of acrylic polymers, styrenated acrylic polymers, acrylic-urethane polymers, vinyl acrylates, polyurethane, polyurethane copolymers, vinyl acetate polymers and vinyl acetate copolymers, olefin polymers and olefin copolymers.

25. The method of claim 20, wherein said aqueous nail enamel composition further includes a coalescing solvent.

26. The method of claim 20, wherein said top coat film forming component has a gloss transition temperature greater than about 95° C.

27. The method of claim 21, wherein said base coat film forming component comprises a solvent based polymer.

28. The method of claim 21, wherein said base coat film forming component comprises an aqueous emulsion or colloidal dispersion polymer or copolymer.

29. A nail enamel composition of non-toxic components for forming an irregular film over a base nail enamel composition applied to natural or synthetic human nails, said composition comprising an aqueous top coat composition including at least one film forming component having a glass transition temperature greater than 0° C. in an aqueous medium, said film forming component forming an irregular film upon drying.

30. The composition of claim 29, wherein said irregular film contains uniform or random cracks therein.

31. The composition of claim 29, wherein said film forming component comprises an aqueous emulsion or colloidal dispersion polymer or copolymer.

32. The composition of claim 29, wherein said film forming component is selected from the group consisting of acrylic polymers, styrenated acrylic polymers, acrylic-urethane polymers, vinyl acrylates, polyurethane, polyurethane copolymers, vinyl acetate polymers and vinyl acetate copolymers, olefin polymers and olefin copolymers.

33. The composition of claim 29, further including a coalescing solvent.

34. The composition of claim 29, further including a plasticizer.

35. The composition of claim 29, further including a pigment or organic colorant.

36. The composition of claim 29, wherein said film forming component has a glass transition temperature greater than about 10° C.

37. The composition of claim 29, wherein said film forming component has a glass transition temperature greater than about 95° C.

38. A method of forming an irregular film over a base nail enamel composition applied to natural or synthetic human nails, said method comprising applying an aqueous top coat composition of non-toxic components including at least one top coat film forming component having a glass transition temperature greater than 0° C. in an aqueous medium over said base nail enamel composition, said top coat film forming component forming an irregular film upon drying.

39. The method of claim 38, wherein said base nail enamel composition of non-toxic components includes at least one base coat film forming component over said natural or synthetic nails, said base coat film forming component forming a film over said natural or synthetic nails.

40. The method of claim 38, wherein said irregular film contains uniform or random cracks therein.

41. The method of claim 38, wherein said top coat film forming component comprises an aqueous emulsion or colloidal dispersion polymer or copolymer.

42. The method of claim 38, wherein said top coat film forming component is selected from the group consisting of acrylic polymers, styrenated acrylic polymers, acrylic-urethane polymers, vinyl acrylates, polyurethane, polyurethane copolymers, vinyl acetate polymers and vinyl acetate copolymers, olefin polymers and olefin copolymers.

43. The method of claim 38, wherein said aqueous top coat composition further includes a coalescing solvent.

44. The method of claim 38, wherein said top coat film forming component has a glass transition temperature greater than about 10° C.

45. The method of claim 38, wherein said top coat film forming component has a glass transition temperature greater than about 95° C.

46. The method of claim 38, wherein said base coat film forming component comprises a solvent based polymer.

47. The method of claim 38, wherein said base coat film forming component comprises an aqueous emulsion or colloidal dispersion polymer or copolymer.

* * * * *

UNITED STATES PATENT AND TRADEMARK OFFICE
CERTIFICATE OF CORRECTION

PATENT NO. : 6,139,822
DATED : October 31, 2000
INVENTOR(S) : Socci, et al.

It is certified that error appears in the above-identified patent and that said Letters Patent is hereby corrected as shown below:

Column 10,
Line 33, insert -- EXAMPLE 8 --.
Line 43, insert -- EXAMPLE 9 --.
Line 52, insert -- EXAMPLE 10 --.
Line 57, insert -- EXAMPLE 11 --.

Column 11,
Line 1, insert -- EXAMPLE 12 --

Column 12,
Line 9, insert -- EXAMPLE 13 --.
Line 20, insert -- EXAMPLE 14 --.
Line 27, insert -- EXAMPLE 15 --.
Line 42, insert -- EXAMPLE 16 --.

Column 14,
Line 60, insert -- EXAMPLE 17 --.

Column 15,
Line 1, insert -- EXAMPLE 18 --.
Line 13, insert -- EXAMPLE 19 --.
Line 22, insert -- EXAMPLE 20 --.
Line 30, insert -- EXAMPLE 21 --.
Line 37, insert -- EXAMPLE 22 --.
Line 45, insert -- EXAMPLE 23 --.
Line 53, insert -- EXAMPLE 24 --.
Line 60, insert -- EXAMPLE 25 --.

Column 16,
Line 1, insert -- EXAMPLE 26 --.
Line 10, insert -- EXAMPLE 27 --.

UNITED STATES PATENT AND TRADEMARK OFFICE
CERTIFICATE OF CORRECTION

PATENT NO. : 6,139,822
DATED : October 31, 2000
INVENTOR(S) : Socci, et al.

It is certified that error appears in the above-identified patent and that said Letters Patent is hereby corrected as shown below:

Column 16,
Line 17, insert -- EXAMPLE 28 --.
Line 28, insert -- EXAMPLE 29 --.
Line 37, insert -- EXAMPLE 30 --.

Column 18,
Line 56, "24" should read -- 20 --.
Line 66, "20" should read -- 23 --.

Signed and Sealed this

Twenty-third Day of October, 2001

Attest:

NICHOLAS P. GODICI
Attesting Officer
Acting Director of the United States Patent and Trademark Office